(12) United States Patent
Sizer et al.

(10) Patent No.: US 10,124,036 B2
(45) Date of Patent: Nov. 13, 2018

(54) LIQUID NUTRITIONAL FORMULA FOR TYROSINEMIA PATIENTS

(71) Applicant: Cambrooke Therapeutics, Inc., Ayer, MA (US)

(72) Inventors: Charles E. Sizer, Lincoln, MA (US); Kurt Olson, Chicago, IL (US); Susan Gingrich, Hamilton, MA (US)

(73) Assignee: Cambrooke Therapeutics, Inc., ayer, MA (US)

( * ) Notice: Subject to any disclaimer, the term of this patent is extended or adjusted under 35 U.S.C. 154(b) by 0 days.

(21) Appl. No.: 14/738,627

(22) Filed: Jun. 12, 2015

(65) Prior Publication Data

US 2016/0361383 A1 Dec. 15, 2016
US 2018/0064784 A9 Mar. 8, 2018

(51) Int. Cl.

| | | |
|---|---|---|
| *A61K 38/17* | (2006.01) | |
| *A61K 31/198* | (2006.01) | |
| *A61K 31/405* | (2006.01) | |
| *A61K 31/4172* | (2006.01) | |
| *A61K 31/20* | (2006.01) | |
| *A61K 31/70* | (2006.01) | |
| *A61K 31/07* | (2006.01) | |
| *A61K 31/375* | (2006.01) | |
| *A61K 31/593* | (2006.01) | |
| *A61K 31/355* | (2006.01) | |
| *A61K 31/122* | (2006.01) | |
| *A61K 31/51* | (2006.01) | |
| *A61K 31/525* | (2006.01) | |
| *A61K 31/675* | (2006.01) | |
| *A61K 31/519* | (2006.01) | |
| *A61K 31/714* | (2006.01) | |
| *A61K 31/197* | (2006.01) | |
| *A61K 31/4188* | (2006.01) | |
| *A23L 2/52* | (2006.01) | |
| *A23L 2/66* | (2006.01) | |

(52) U.S. Cl.
CPC ............ *A61K 38/1709* (2013.01); *A23L 2/52* (2013.01); *A23L 2/66* (2013.01); *A61K 31/07* (2013.01); *A61K 31/122* (2013.01); *A61K 31/197* (2013.01); *A61K 31/198* (2013.01); *A61K 31/20* (2013.01); *A61K 31/355* (2013.01); *A61K 31/375* (2013.01); *A61K 31/405* (2013.01); *A61K 31/4172* (2013.01); *A61K 31/4188* (2013.01); *A61K 31/51* (2013.01); *A61K 31/519* (2013.01); *A61K 31/525* (2013.01); *A61K 31/593* (2013.01); *A61K 31/675* (2013.01); *A61K 31/70* (2013.01); *A61K 31/714* (2013.01); *A23V 2002/00* (2013.01)

(58) Field of Classification Search
CPC ........ A23L 33/17; A23L 33/175; A23L 33/18; A23L 33/185; A23L 33/19; A61K 38/018
See application file for complete search history.

(56) References Cited

U.S. PATENT DOCUMENTS

| | | | |
|---|---|---|---|
| 4,414,238 A | | 11/1983 | Schmidl |
| 5,587,399 A | * | 12/1996 | Acosta ................... A23L 33/175 424/601 |
| 5,922,766 A | | 7/1999 | Acosta et al. |
| 8,604,168 B2 | | 12/2013 | Ney et al. |
| 9,414,619 B2 | | 8/2016 | Sizer et al. |
| 2008/0026105 A1 | * | 1/2008 | Khatib ..................... A23L 33/12 426/72 |
| 2010/0317562 A1 | | 12/2010 | Paolella et al. |
| 2010/0317597 A1 | * | 12/2010 | Ney ..................... A61K 38/018 514/20.9 |
| 2013/0196024 A1 | | 8/2013 | Ney et al. |
| 2014/0248414 A1 | | 9/2014 | Ney et al. |

FOREIGN PATENT DOCUMENTS

WO WO 2014/171813 A1 10/2014

OTHER PUBLICATIONS

Murphy et al. "The potential for sodium hexametaphosphate (SHMP) found in common children drinks to limit acid production in the oral biofilm" Journal of Dentistry, vol. 35, Issue 3, Mar. 2007, pp. 214-217.*

Raghuveer et al., Inborn errors of metabolism in infancy and early childhood: an update. Am Fam Physician. Jun. 1, 2006;73(11):1981-90.

* cited by examiner

*Primary Examiner* — Christina Bradley
(74) *Attorney, Agent, or Firm* — Wolf, Greenfield & Sacks, P.C.

(57) ABSTRACT

Liquid metabolic formulas for dietary management of tyrosinemia, including nutritional formulas and hydration beverages (sport drinks).

11 Claims, 6 Drawing Sheets

LIQUID NUTRITIONAL FORMULA FOR TYROSINEMIA PATIENTS

BACKGROUND

Tyrosinemia is a genetic disorder characterized by elevated blood levels of the amino acid tyrosine. Tyrosinemia is caused by deficiency of tyrosine metabolism, which leads to increased levels of tyrosine and tyrosine products in the body. There are three types of tyrosinemia, classed by the particular enzyme deficiency of the patient. Type 1 tyrosinemia, also known as hepatorenal tyrosinemia, is the most severe form of the disease and is caused by a deficiency of the enzyme fumarylacetoacetate hydrolase, which catalyzes the final step in tyrosine metabolism. Type 1 tyrosinemia can lead to liver and kidney failure, problems affecting the nervous system and increased risk of liver cancer. Type 2 tyrosinemia is caused by a deficiency of the enzyme aminotransferase and affects the eyes, skin and mental development. Type 3 tyrosinemia is the rarest form and is caused by a deficiency of the enzyme 4-hydroxyphenylpyruvate dioxygenase. Type 3 tyrosinemia is characterized by intellectual disability, seizures and intermittent ataxia.

Treatment of tyrosinemia typically involves a diet that is low in phenylalanine and low in tyrosine (low Phe/Tyr). However in children, the low Phe/Tyr diet must also be designed to provide enough of the two amino acids to support growth while avoiding excesses of both. This low Phe/Tyr diet must be consumed for life and compliance is an issue for many. Treatment may also include the administration of nitisinone, a medication that blocks the formation of fumarylacetoacetate.

SUMMARY

Nutritional Formulation

Described herein are metabolic formulas for the dietary management of tyrosinemia. In one embodiment, the metabolic formulation is a nutritional formula (also referred to as a nutritional formulation) that has a balanced amino acid profile suitable for therapy for individuals who have tyrosinemia; they include complete, peptide-based, ready-to-drink (RTD) nutritional formulas, such as shelf-stable, ready-to-drink (liquid), nutritional formulas that have a balanced amino acid profile and are suitable therapy for patients suffering from tyrosinemia. The RTD nutritional formulas can be packaged using known methods. For example, the container can be a bottle, a carton or a can. In some embodiments, packaging is carried out under aseptic conditions. The RTD formula can be canned (e.g. placed in containers that are then hermetically sealed and sterilized, such as by heat) or bottled. In some embodiments, the formula is bottled by a hot fill bottling process.

In a second embodiment, the metabolic formula is a hydration beverage (also referred to as a sports drink).

The nutritional formulas have a balanced amino acid profile suitable for therapy for individuals who have tyrosinemia, are low in phenylalanine and tyrosine, have a lower osmolality than a purely synthetic amino acid formula and have an acceptable taste. For example, the osmolality of a nutritional formula described herein is generally about 330 milliosmoles per liter. In contrast, the osmolality of purely synthetic amino acid formulas is generally about 1000 milliosmoles per liter.

The nutritional formula comprises in one embodiment: (a) a protein source that comprises (i) whey protein, such as caseino-glyco-macropeptide (cGMP) and (ii) complementary essential amino acids which are a mixture of arginine, tryptophan, leucine, histidine and cysteine and provides a balanced amino acid profile; (b) a carbohydrate source, which typically includes non-reducing sugars to minimize/reduce browning potential; (c) a fat (lipid/oil) source; and (d) vitamins and minerals in sufficient quantities to meet the daily requirements for each. In alternative embodiments, in (ii) the complimentary essential amino acids are a mixture of arginine, tryptophan, leucine, histidine and methionine or the complimentary essential amino acids are a mixture of arginine, tryptophan, leucine, histidine, cysteine and methionine. The nutritional formula comprises no added tyrosine or phenylalanine; tyrosine and phenylalanine in the nutritional formula are contributed by cGMP.

In addition, the nutritional formula typically, but optionally, includes flavors, which can be natural or artificial or a combination of both; coloring agents, which can be natural or artificial or a combination of both; sweetener, which can be natural or artificial or a combination of both; gelling agents, thickening agents, stabilizing agents, sequestrants, emulsifiers or a combination of two or more of gelling agents, thickening agents, stabilizing agents, sequestrants, emulsifiers, each of which can be natural or artificial or a combination of both.

In one embodiment, the nutritional formula comprises: water, sucrose, whey protein isolate, vitamin and mineral blend (dicalcium phosphate, calcium lactate, dipotassium phosphate, choline bitartrate, magnesium citrate, sodium ascorbate and ascorbic acid, ferrous sulfate, zinc sulfate, niacinamide, vitamin E dl-alphatocopheryl acetate, calcium d-pantothenate, manganese sulfate, vitamin A palmitate, vitamin B6 pyridoxine, riboflavin, thiamin hydrochloride, copper gluconate, folic acid, potassium iodide, vitamin K 1 phytonadione, sodium selenite, sodium molybdate, chromium chloride, biotin, vitamin D3 cholecalciferol, vitamin B12 cyanocobalamin), food starch modified, leucine, maltodextrin, cocoa butter, canola oil, arginine, cellulose gel and carboxymethylcellulose sodium, natural flavor (propylene glycol, ethyl alcohol, water, polysorbate 80 potassium sorbate), histidine, one or more food grade polyphosphate chelator, such as sodium hexametaphosphate, cysteine, tryptophan, carrageenan, sodium stearoyl lactylate.

Also described are methods for producing the nutritional formula described herein. One embodiment of the method is represented schematically in FIG. 1. In one embodiment, the method comprises: (a) kitting together dry ingredients; (b) kitting together a mineral mixture; (c) producing an oil incorporation mixture; (d) combining, in order, the mixtures produced in steps (a) to (c) in a high shear blender under conditions under which a stable emulsion formula is formed; (e) adding vitamin C to the formula (emulsion); (f) sterilizing the formula by ultra-high temperature aseptic treatment of the emulsion under conditions sufficient to sterilize the formula, for example at 140° C. for 5-6 seconds; (g) optionally, storing the sterilized formula in an aseptic storage tank; and (h) aseptically packaging the formula.

Hydration Beverage

In some embodiments, the metabolic formula is a hydration beverage or sports drink for dietary management of individuals who have tyrosinemia. The hydration beverage or sports drink comprises: (a) a protein source that comprises (i) caseino-glyco-macropeptide (cGMP) and (ii) complementary essential amino acids which are a mixture of arginine, tryptophan, leucine, histidine and cysteine, and provides a balanced amino acid profile; (b) a carbohydrate source, which typically includes non-reducing sugars to minimize/reduce browning potential; and (c) vitamins and minerals. In addition, the hydration beverage or sports drink typically, but optionally, includes preservatives; flavors, which can be natural or artificial or a combination of both; coloring agents, which can be natural or artificial or a combination of both; sweetener, which can be natural or artificial or a combination of both; gelling agents, thickening agents, stabilizing agents, sequestrants, emulsifiers or a combination of two or more of gelling agents, thickening agents, stabilizing agents, sequestrants, emulsifiers, each of which can be natural or artificial or a combination of both. In one specific embodiment, the hydration beverage or sports drink comprises the components listed in Table 3. In one specific embodiment, the hydration beverage or sports drink comprises the components listed in Table 4. In a specific embodiment, the hydration beverage consists essentially of the components listed in Table 3 or consists essentially of the components listed in Table 4.

In a specific embodiment, the hydration beverage or sports drink comprises: water, sugar (e.g., sucrose), a protein source, such as whey protein isolate (glycomacropeptide), citric acid, amino acids (e.g., leucine, arginine, histidine, cysteine, tryptophan), sodium citrate, natural flavors, (ethyl alcohol, natural flavors, propylene glycol, glycerine, polysorbate 60, citric acid), potassium sorbate (preservative), sodium benzoate (preservative), vitamin/mineral blend (sugar, niacin [vitamin b3], pantothenate [vitamin b5], pyridoxine [vitamin b6], riboflavin [vitamin b2], folic acid, biotin, cyanocobalamin [vitamin b12]), FD&C yellow #5, FD&C red #40. The hydration beverage or sports drink may optionally include flavors, which can be natural or artificial or a combination of both; coloring agents, which can be natural or artificial or a combination of both; sweetener, which can be natural or artificial or a combination of both; gelling agents, thickening agents, stabilizing agents, sequestrants, emulsifiers or a combination of two or more of gelling agents, thickening agents, stabilizing agents, sequestrants, emulsifiers, each of which can be natural or artificial or a combination of both.

The hydration beverage or sports drink described herein is produced, using methods also described herein and other methods known to those of skill in the art. In one embodiment, the method comprises: (a) kitting together the dry ingredients; (b) blending together with the kitted dry ingredients in the following order (i) preservatives, (ii) a carbohydrate source (such as sucrose), (iii) a protein source (such as cGMP), (iv) amino acids (e.g., leucine, arginine, histidine, cysteine, tryptophan) with buffers and citric acid, (v) flavorings, (vi) coloring, and (vii) sweeteners to form a hydration beverage; (c) titrating the pH of the hydration beverage; (d) optionally, ultra-heat treating the hydration beverage; (e) bottling the hydration beverage by a hot fill bottling process; and, (f) cooling the bottled hydration beverage in a cool water bath. In some embodiments, the bending is performed at ambient temperature (e.g., room temperature). In some embodiments, the blending, pH titrating and ultra-heat treating are performed while the hydration beverage is being continuously mixed. In some embodiments the preservatives are sorbate and benzoate. In some embodiments, the amount of sorbate ranges from about 0.05 g to about 1.0 g per 1030.4158 g of hydration beverage. In some embodiments, the amount of benzoate ranges from about 0.05 g to about 1.0 g per 1030.4158 g of hydration beverage. In some embodiments, the hydration beverage pH is titrated to between about pH 4.0 and about pH 5.0. In some embodiments, the hydration beverage pH is titrated to between about pH 4.3 and about pH 4.4.

DETAILED DESCRIPTION

Dietary compliance is the primary issue for tyrosinemia patients whose diets are based on amino acid formulas. Compliance is an issue and there have been many attempts to improve acceptance of foods and beverages for those with tyrosinemia but those efforts have not been successful.

Ready-to-drink, shelf-stable formulae, such as beverages, pose particular challenges, at least in part because the components essential for complete sustenance components must be combined to produce the nutritional formula in such a way that they remain dissolved, suspended or otherwise retained in the formula (beverage). This is a challenge because each ingredient in the nutritional formula has unique requirements for making it stable. Particularly difficult to incorporate is the caseino-glycomacro-peptide, which contains sialic acid attached to an amino acid residue on the chain. This sialic acid reduces the isoelectric point of the peptide as a function of the fraction of sites occupied by sialic acid. Thus, the isoelectric point can change as the peptide is being processed. Peptides are not soluble at or near their isoelectric pH and tend to precipitate or gel. Described herein is a method by which nutritional formulas described are made, with the result that the formula is ready-to-drink and shelf-stable.

Nutritional Formula Preparation

Figure 1:
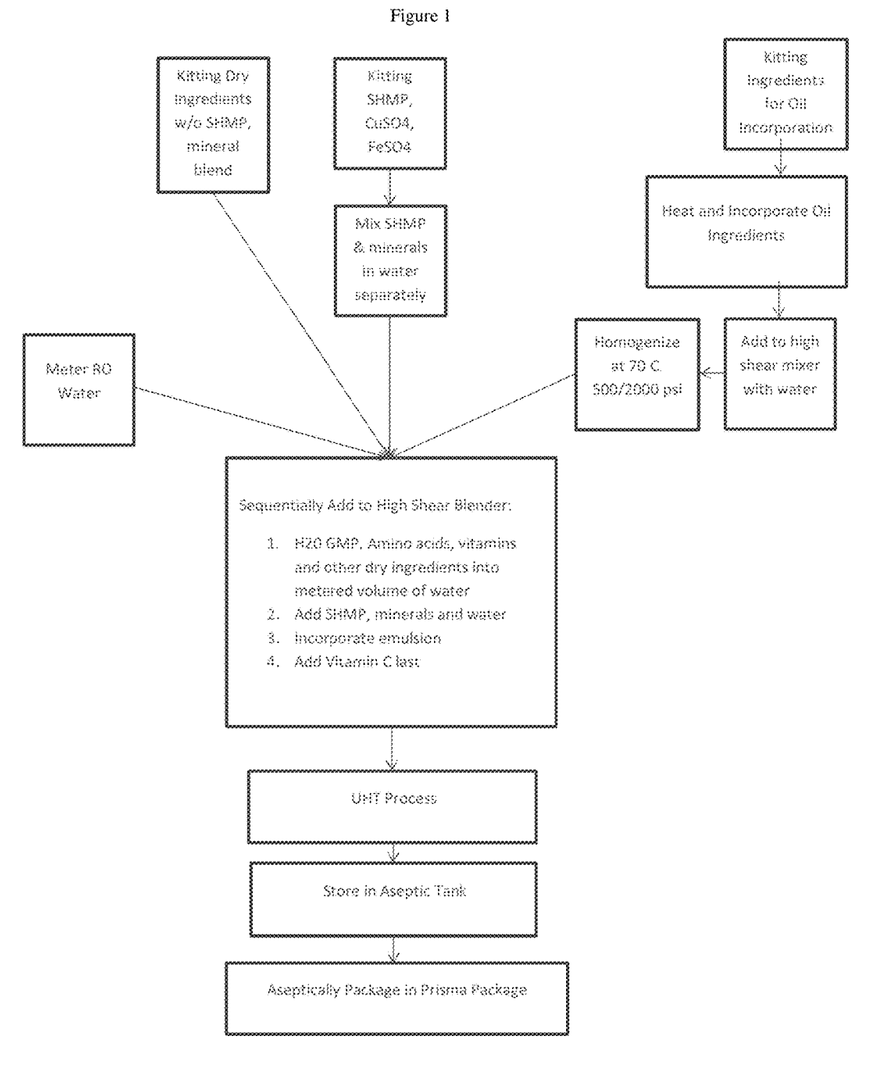
FIG. 1 is a schematic representation of a method by which nutritional formulas are produced.
Figure 2:
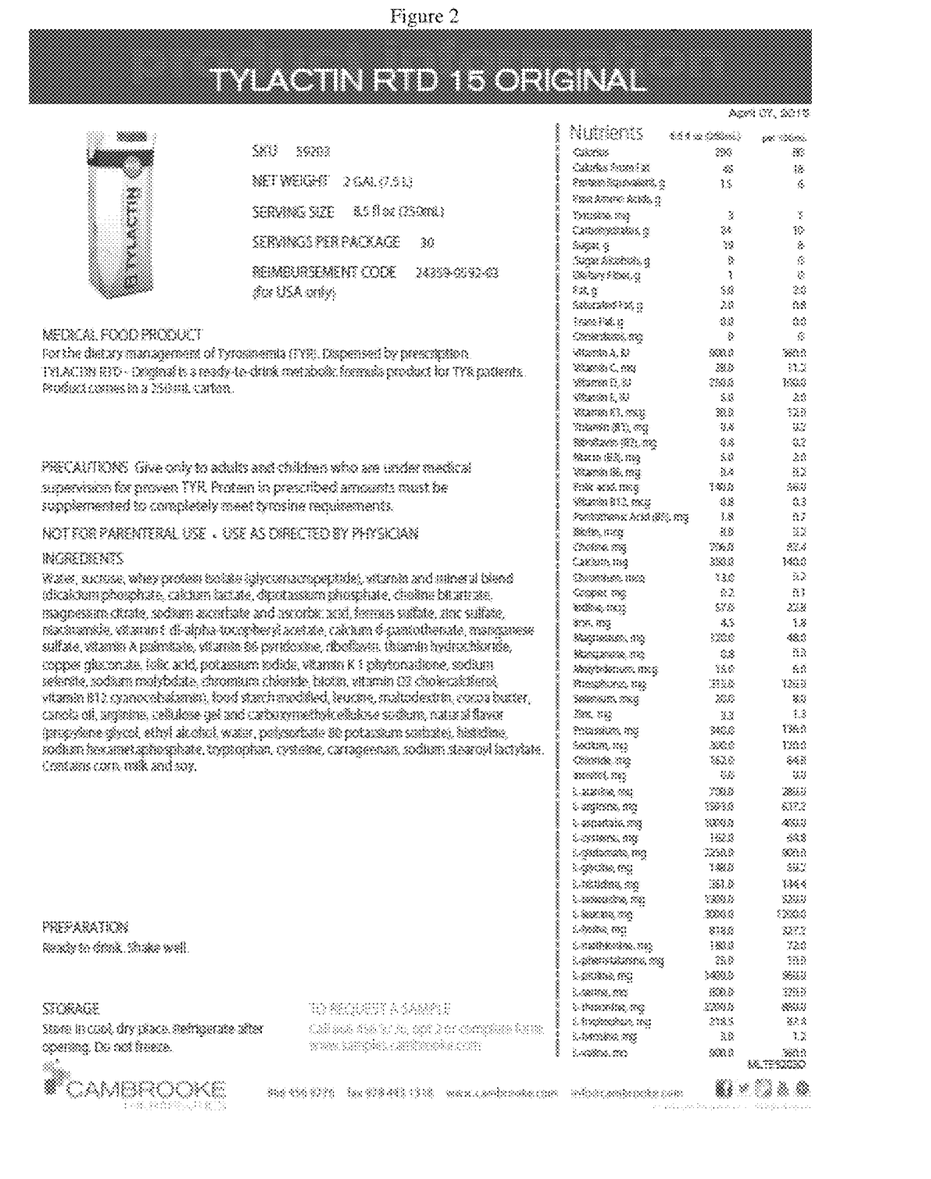
FIG. 2 is a label for TYLACTIN RTD 15 ORIGINAL
Figure 3:
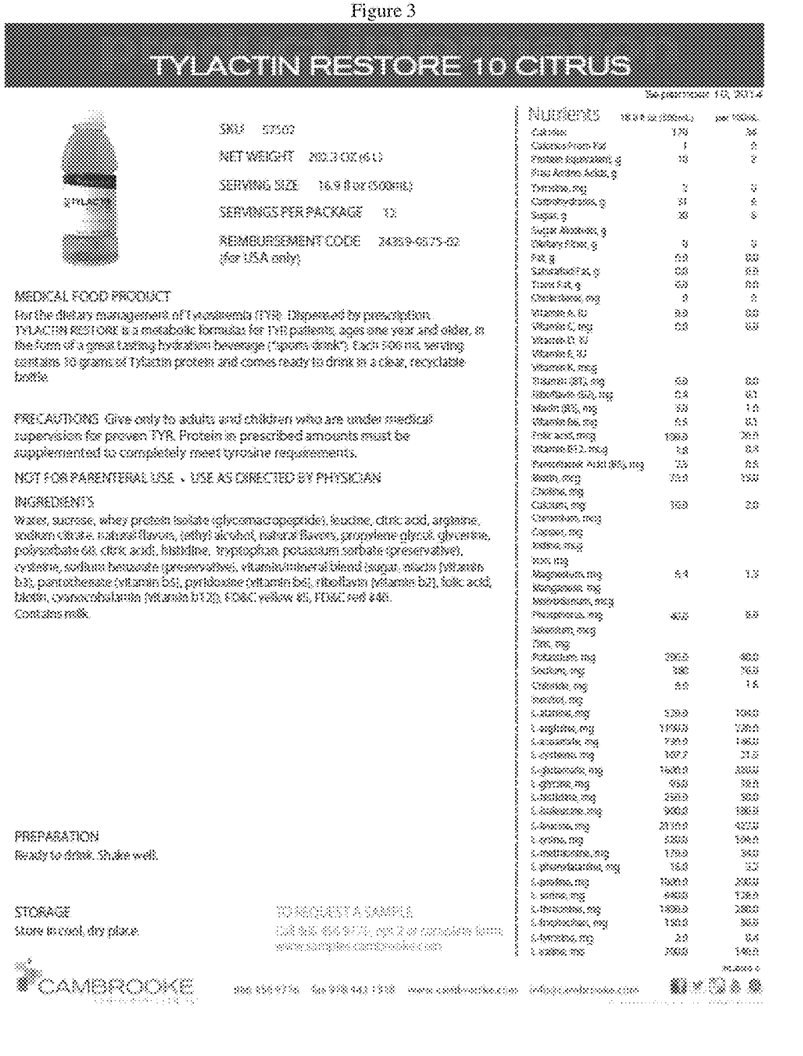
FIG. 3 is a label for TYLACTIN RESTORE 10 CITRUS
Figure 4:
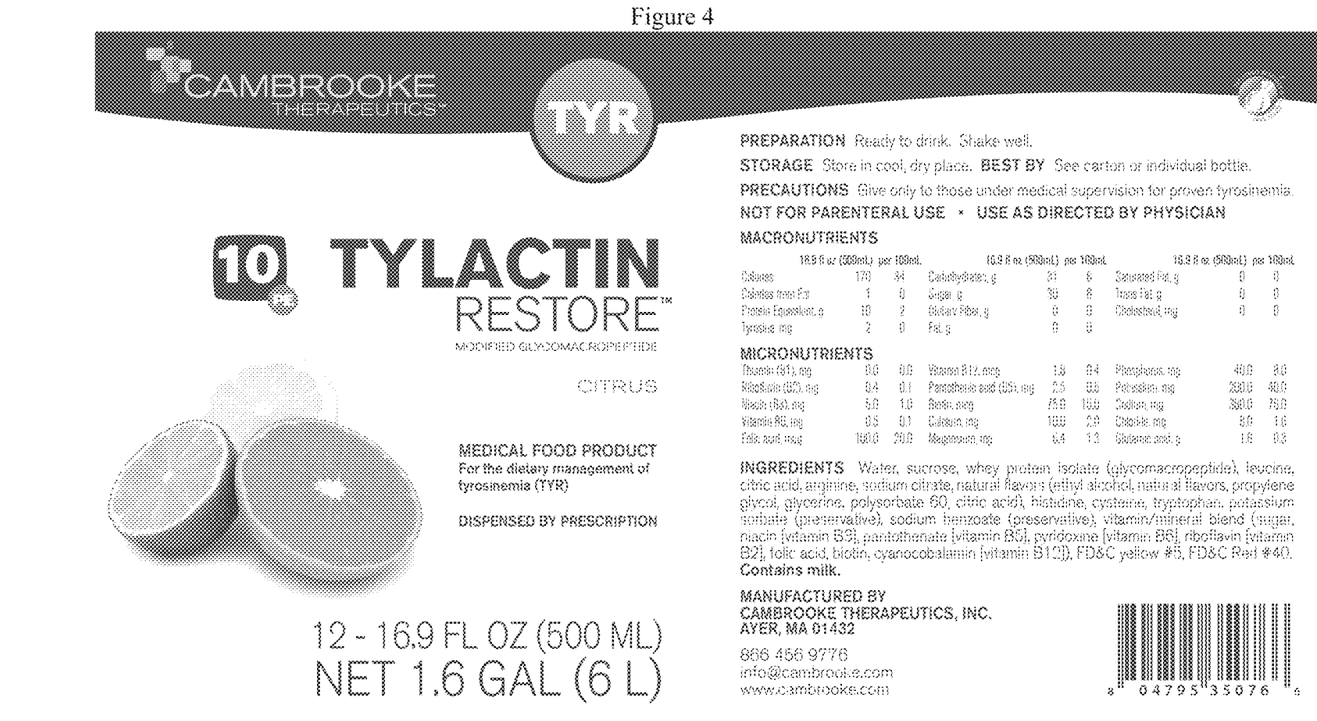
FIG. 4 is a label for TYLACTIN RESTORE CITRUS
Figure 5:
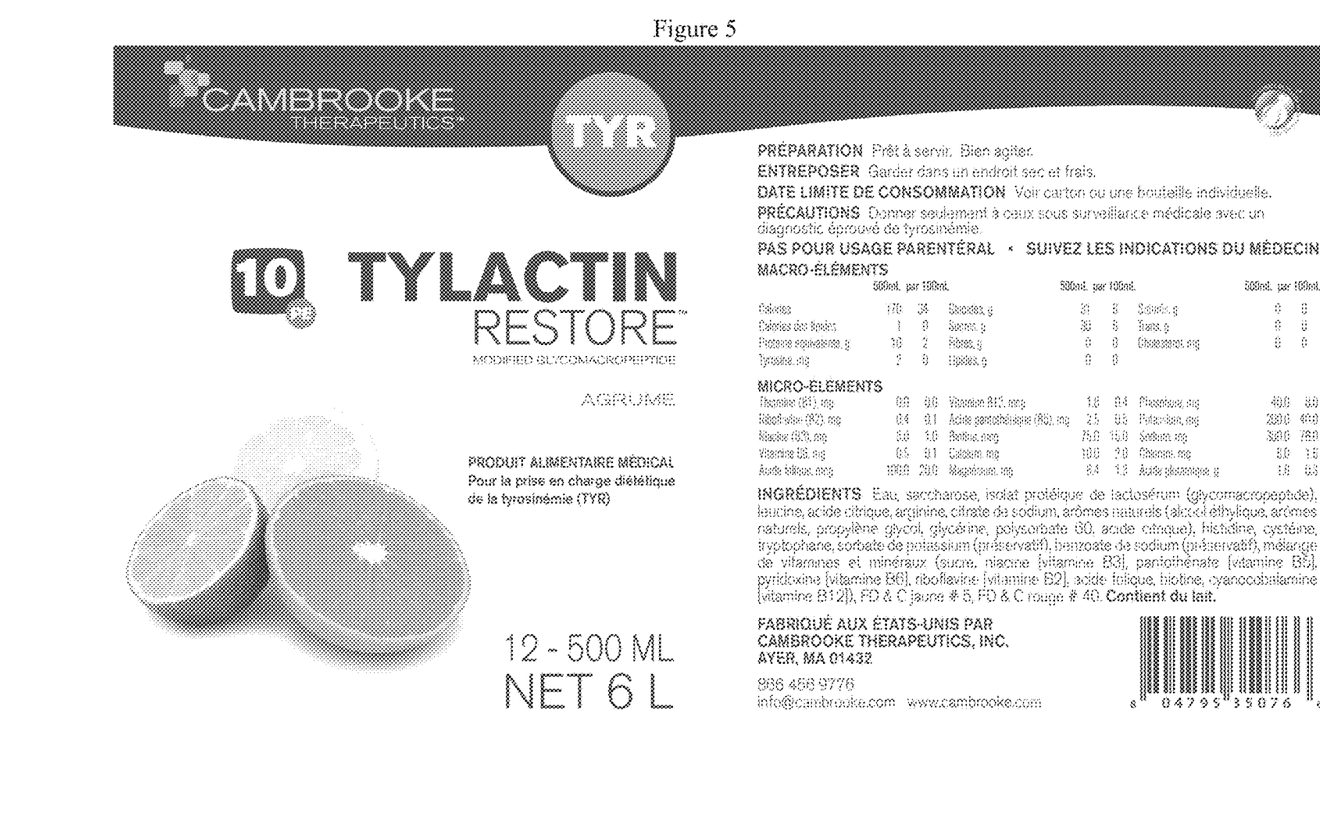
FIG. 5 is a label for TYLACTIN RESTORE (FRENCH)
Figure 6:
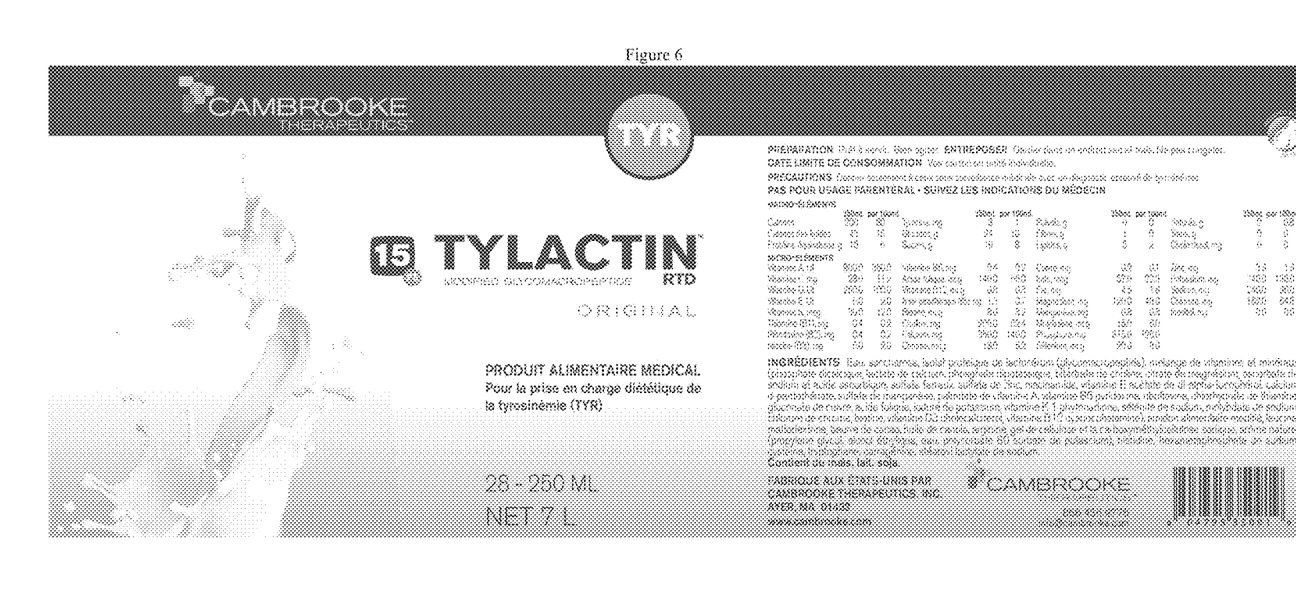
FIG. 6 is a label for TYLACTIN RTD ORIGINAL

Nutritional formula preparation is carried out using the method represented schematically in the Figure. Kitting of ingredients is carried out as indicated: Kitting of dry ingredients, to produce a dry ingredient mixture, is carried out by combining dry ingredients without food grade polyphosphate chelator, such as sodium hexametaphosphate (SHMP), or mineral blend; kitting together of food grade polyphosphate chelator, such as SHMP, $CuSO_4$, $FeSO_4$ and, if needed, other minerals; and kitting of ingredients for oil incorporation. The SHMP and minerals are mixed in water separately. Ingredients for oil incorporation are heated and incorporated together. These include octenyl succinate starch (OSS), sodium stearoyl lactylate (SSL), cocoa butter, vegetable oil and other oil-soluble ingredients. They are subjected to high shear and homogenization. The resulting three combinations (see the Figure) are combined with water and other components as shown in FIG. 1 and subjected to the conditions shown, beginning with the step "Sequentially add to high shear blender". The resulting formula is packaged, such as aseptically or by canning. In some embodiments, the dry ingredients include caseino glycomacropeptides (GMP), amino acids, and vitamins.

SHMP is combined with minerals, such as a metal fortification mixture, which comprises at least one type of metallic ions to produce a SHMP-minerals in water SHMP-metal mixture. In some embodiments, the metal fortification mixture comprises two or more types of metallic ions. In some embodiments, the metallic ions are copper (e.g., $Cu^{2+}$)

and/or iron (e.g., $Fe^{2+}$) and/or Zinc ($Zn^{+2}$). In some embodiments, the metallic ions are from sources such as $CuSO_4$ and/or $FeSO_4$ and/or $ZnSO_4$. In some embodiments, a sequestrant or chelator other than a food grade polyphosphate chelator such as SHMP, is combined with minerals. Sequestrants include but are not limited to Calcium disodium ethylene diamine tetra-acetate (E385), Glucono delta-lactone (E575), Potassium gluconate (E577), Sodium gluconate (E576), Sodium triphosphate and EDTA.

An emulsion is prepared by combining and heating oil ingredients, which includes modified starch, sodium stearoyl lactylate (SSL), oils such as cocoa butter and vegetable oil, and other oil soluble ingredients. The modified starch used herein is an amphiphilic starch, which is hydrophilic and hydrophobic in nature. The modified starch is used to bind to fat to prevent the fat from interacting with the proteins by steric hindrance. For example, a normally hydrophilic starch is modified to incorporate hydrophobic moieties such as octenyl groups which binds to fats. The resulting modified starch has an amphiphilic nature and thus surface active properties which are useful in stabilizing oil/water emulsions. In some embodiments, the modified starch is octenyl succinate starch (OSS) or another amphiphilic starch. The hydrophobic octenyl moiety binds the fats in the emulsion assuring that the starch remains attached to the fat globule, preventing the fats from interacting with the proteins by steric hindrance.

The heated and combined oil ingredients are then added to a mixer, such as a high shear mixer, with water and are homogenized to form an emulsion. In some embodiments, the oil ingredients are homogenized with water at about 60-80° C. and about 400 psi to about 3000 psi. In some embodiments, the oil ingredients are homogenized in two steps. In some embodiments, the first emulsion step is performed at between about 60° C. and about 80° C. and at a pressure between about 1200 psi and 3000 psi. In some embodiments, the second emulsion step is performed at between about 60° C. and about 80° C. and at a pressure between about 300 psi and about 700 psi. In one embodiment, the oil ingredients is homogenized at about 70° C. and about 500 psi to about 2000 psi.

As shown, the mixtures are sequentially added to a blender such as a high shear blender in the following order: the dry ingredient mixture is mixed into metered volume of water, the fortified SHMP mixture is added, the emulsion is incorporated, and vitamin C is added last. In some embodiments, the vitamin C is sodium ascorbate and/or ascorbic acid. In some embodiments, the amount of vitamin C added is between about 120 mg and about 450 mg. In some embodiments, the final amount of vitamin C present in the formula is equal to 50% of the recommended daily allowance (RDA) of vitamin C. The combined mixture is subjected to ultra-high temperature processing (UHT). The resulting formula is subsequently placed/stored in aseptic tank and then aseptically packaged. In some embodiments, the aseptic packaging is a Prisma package. In some embodiments, the aseptic packaging is a can.

Hydration Beverage Preparation

Hydration beverage or sports drink preparation is carried out using the method described herein. In one embodiment, the method comprises: (a) kitting together the dry ingredients; (b) blending together with the kitted dry ingredients in the following order (i) preservatives, (ii) a carbohydrate source (e.g., sucrose), (iii) a protein equivalent source (e.g., cGMP), (iv) amino acids (e.g., leucine, arginine, histidine, cysteine, tryptophan) with buffers and citric acid, (v) flavorings, (vi) coloring, and (vii) sweeteners to form a hydration beverage; (c) titrating the pH of the hydration beverage; (d) ultra-heat treating the hydration beverage; (e) bottling the hydration beverage by a hot fill bottling process; and, (f) cooling the bottled hydration beverage in a cool water bath. In some embodiments, the bending is performed at ambient temperature (e.g., room temperature). In some embodiments, the blending, pH titrating and ultra-heat treating are performed while the hydration beverage is being continuously mixed. In some embodiments, the hydration beverage pH is titrated to between about pH 4.0 and about pH 5.0. In some embodiments, the hydration beverage pH is titrated to between about pH 4.3 and about pH 4.4.

Example 1: Preparation of Complete Nutritional Formulation

Dry ingredient mixture was prepared by kitting together the dry ingredients without sodium hexametaphosphate (SHMP), vitamins, or mineral. Table 1 lists dry ingredients used, such as whey protein isolate (such as caseino glycomacropeptides (GMP)), amino acids, vitamins, sugar, dextrin, natural flavoring products, natural food coloring, sodium chloride, cellulose gum, carrageenan, and sweeteners. In another step, SHMP is combined with a copper and iron fortification mixture. In another step, vitamins and minerals are mixed together in water to provide a vitamin and mineral fortification mixture. Subsequently, the SHMP with the copper and iron fortification mixture is mixed with the vitamin and mineral fortification mixture, thereby forming a metal/mineral fortified SHMP mixture.

In a separate step, an emulsion is prepared by combining and heating oil ingredients.

The foregoing mixtures are then sequentially added to a blender such as a high shear blender in the following order: the dry ingredient mixture is mixed into metered volume of water, the fortified SHMP mixture is added, the emulsion is incorporated, and Vitamin C (sodium ascorbate and ascorbic acid) is added last. The table below provides the amounts of each ingredient used to prepare the formula. The combined mixture is subjected to ultra-high temperature processing (UHT) at about 140° C. for about 5 to about 6 seconds The resulting formula is subsequently stored in aseptic tank and then aseptically packaged using Prisma Packages.

TABLE 1

Tylactin RTD Original
Tylactin RTD Original
Number of 250 ml Servings: 4
Weight: 1064 g

|  | Range | Units | % Weight Range |
|---|---|---|---|
| Water | 635-955 | Gram |  |
| Caseino glycomacropeptides (GMP) | 40-60 | Gram | 3.76-5.64 |
| Vitamin and mineral fortification | 16-25 | Gram | 1.5-2.35 |
| Amino Acids | 16-25 | Gram | 1.5-2.35 |
| Sugar | 56-84 | Gram | 5.26-7.89 |
| dextrin sweetener | 8-12 | Gram | 0.75-1.13 |
| Emulsion | 72-108 | Gram | 6.77-10.15 |
| Natural flavors | 2.4-3.6 | Gram | 0.23-0.34 |
| Natural color | 0.4-0.6 | Gram | 0.04-0.06 |
| sodium hexametaphosphate | 1-2 | Gram | 0.09-0.19 |
| cellulose gum | 3.8-6 | Gram | 0.36-0.56 |
| carrageenan | 0.2-0.5 | Gram | 0.02-0.05 |
|  | .05-1.0 | Gram | 0.004-0.09 |
|  | .05-1.0 | Gram | 0.004-0.09 |

TABLE 2

Tylactin RTD 15 Original

| TYLACTIN RTD 15 ORIGINAL | per serving 8.5 fl oz (250 mL) | Range | % Weight Range | per 100 mL |
|---|---|---|---|---|
| Nutrients | | | | |
| Calories | 200 | 160-240 | | 80 |
| Calories From Fat | 45 | 36-54 | | 18 |
| Protein Equivalent, g | 15 | 12-18 | 4.51-6.77 | 6 |
| Free Amino Acids, g | | 0 | | |
| Tyrosine, mg | 3 | 2.4-3.6 | <.01% | 1 |
| Carbohydrates, g | 24 | 19.2-28.8 | 7.22-10.83 | 10 |
| Sugar, g | 19 | 15.2-22.8 | 5.71-8.57 | 8 |
| Sugar Alcohols, g | 0 | 0 | | 0 |
| Dietary Fiber, g | 1 | 0.8-1.2 | 0.30-0.45 | 0 |
| Fat, g | 5 | 4-6 | 1.50-2.26 | 2 |
| Saturated Fat, g | 2 | 1.6-2.4 | 0.60-0.90 | 0.8 |
| Trans Fat, g | 0 | 0 | | 0 |
| Cholesterol, mg | 0 | 0 | | 0 |
| Vitamin A, IU (mcg) | 900 (495 mcg) | 720-1080 (396-594 mcg) | <0.01% | 360 |
| Vitamin C, mg | 28 | 22.4-33.6 | 8.42-12.63 | 11.2 |
| Vitamin D, IU (mcg) | 250 (6.25 mcg) | 200-300 (5-7 mcg) | <0.01% | 100 |
| Vitamin E, IU | 5 (5 mg) | 4-6 (4-6 mg) | <0.01% | 2 |
| Vitamin K, mcg | 30 | 24-36 | <0.01% | 12 |
| Thiamin (B1), mg | 0.4 | 0.32-0.48 | <0.01% | 0.2 |
| Riboflavin (B2), mg | 0.4 | 0.32-0.48 | <0.01% | 0.2 |
| Niacin (B3), mg | 5 | 4-6 | <0.01% | 2 |
| Vitamin B6, mg | 0.4 | 0.32-0.48 | <0.01% | 0.2 |
| Folic acid, mcg | 140 | 112-168 | <0.01% | 56 |
| Vitamin B12, mcg | 0.8 | 0.64-0.96 | <0.01% | 0.3 |
| Pantothenic Acid (B5), mg | 1.8 | 1.44-2.16 | <0.01% | 0.7 |
| Biotin, mcg | 8 | 6.4-9.6 | <0.01% | 3.2 |
| Choline, mg | 206 | 164.8-247.2 | 0.06-0.09 | 82.4 |
| Calcium, mg | 350 | 280-420 | 0.11-0.16 | 140 |
| Chromium, mcg | 13 | 10.4-15.6 | <0.01% | 5.2 |
| Copper, mg | 0.2 | 0.16-0.24 | <0.01% | 0.1 |
| Iodine, mcg | 57 | 45.6-68.4 | <0.01% | 22.8 |
| Iron, mg | 4.5 | 3.6-5.4 | <0.01% | 1.8 |
| Magnesium, mg | 120 | 96-144 | 0.04-0.05 | 48 |
| Manganese, mg | 0.8 | 0.64-0.96 | <0.01% | 0.3 |
| Molybdenum, mcg | 15 | 12-18 | <0.01% | 6 |
| Phosphorus, mg | 315 | 252-378 | 0.09-0.14 | 126 |
| Selenium, mcg | 20 | 16-24 | <0.01% | 8 |
| Zinc, mg | 3.3 | 2.64-3.96 | <0.01% | 1.3 |
| Potassium, mg | 340 | 272-408 | 0.10-0.15 | 136 |
| Sodium, mg | 300 | 240-360 | 0.09-0.14 | 120 |
| Chloride, mg | 162 | 129.6-194.4 | 0.05-0.07 | 64.8 |
| Inositol, mg | 0 | 0 | 0.00-0.00 | 0 |
| L-alanine mg | 700 | 560-840 | 0.21-0.32 | 280 |
| L-arginine mg | 1593 | 1274.4-1911.6 | 0.48-0.72 | 637.2 |
| L-aspartate mg | 1000 | 800-1200 | 0.30-0.45 | 400 |
| L-cysteine, mg | 162 | 129-194 | 0.05-0.07 | 64.8 |
| L-glutamate, mg | 2250 | 1800-2700 | 0.68-1.01 | 900 |
| L-glycine, mg | 148 | 118.4-177.6 | 0.04-0.07 | 59.2 |
| L-histidine, mg | 361 | 288.8-433.2 | 0.11-0.16 | 144.4 |
| L-isoleucine, mg | 1300 | 1040-1560 | 0.39-0.59 | 520 |
| L-leucine, mg | 3000 | 2400-3600 | 0.90-1.35 | 1200 |
| L-lysine, mg | 818 | 654.4-981.6 | 0.25-0.37 | 327.2 |
| L-methionine, mg | 180 | 144-216 | 0.05-0.08 | 72 |
| L-phenylalanine, mg | 25 | 20-30 | 0.01-0.01 | 10 |
| L-proline, mg | 1400 | 1120-1680 | 0.42-0.63 | 560 |
| L-serine, mg | 800 | 640-960 | 0.24-0.36 | 320 |
| L-threonine, mg | 2200 | 1760-2640 | 0.66-0.99 | 880 |
| L-tryptophan, mg | 218 | 174.4-261.6 | 0.07-0.10 | 87.4 |
| L-tyrosine, mg | 3 | 2.4-3.6 | | 1.2 |
| L-valine, mg | 900 | 720-1080 | 0.27-0.41 | 360 |

TABLE 3

Tylactin Restore 10 Citrus
Tylactin Restore 10 Citrus
Number of Servings: 2 (515 g per serving)
Weight: 1030 g

| | Range | Measure | % Weight Range |
|---|---|---|---|
| Water | 752-1129 | Gram | |
| (Vitamins and minerals) | 0.06-0.08 | Gram | 0.01-0.01 |
| Complementary Amino Acids | 5.6-8.4 | Gram | 0.54-0.82 |
| Caseinglycomacropeptides | 12.8-19.2 | Gram | 1.24-1.86 |

TABLE 4

Tylactin Restore 10 Citrus
Tylactin Restore 10 Citrus

| Nutrients | per serving 16.9 fl oz (500 mL) | Range | % Weight Range | per 100 mL |
|---|---|---|---|---|
| Calories | 170 | 136-204 | | 34 |
| Calories From Fat | 1 | 0.8-1.2 | | 0 |
| Protein Equivalent, g | 10 | 8-10 | 0.78-1.16 | 2 |
| Free Amino Acids, g | | | | |
| Tyrosine, mg | 2 | 1.6-2.4 | <0.01% | 0 |
| Carbohydrates, g | 31 | 24-38 | 2.41-3.61 | 6 |
| Sugar, g | 30 | 24-36 | 2.33-3.49 | 6 |
| Sugar Alcohols, g | | | | |
| Dietary Fiber, g | 0 | | | 0 |
| Fat, g | 0 | | | 0 |
| Saturated Fat, g | 0 | | | 0 |
| Trans Fat, g | 0 | | | 0 |
| Cholesterol, mg | 0 | | | 0 |
| Vitamin A, IU | 0 | | | 0 |
| Vitamin C, mg | 0 | | | 0 |
| Vitamin D, IU | | | | |
| Vitamin E, IU | | | | |
| Vitamin K, mcg | | | | |
| Thiamin (B1), mg | 0 | | | 0 |
| Riboflavin (B2), mg | 0.4 | 0.32-0.48 | <0.01% | 0.1 |
| Niacin (B3), mg | 5 | 42100 | <0.01% | 1 |
| Vitamin B6, mg | 0.5 | 0.4-0.6 | <0.01% | 0.1 |
| Folic acid, mcg | 100 | 80-120 | <0.01% | 20 |
| Vitamin B12, mcg | 1.8 | 1.44-2.16 | <0.01% | 0.4 |
| Pantothenic Acid (B5), mg | 2.5 | 42038 | <0.01% | 0.5 |
| Biotin, mcg | 75 | 60-90 | <0.01% | 15 |
| Choline, mg | | | | |
| Calcium, mg | 10 | 42228 | | 2 |
| Chromium, mcg | | | | |
| Copper, mg | | | | |
| Iodine, mcg | | | | |
| Iron, mg | | | | |
| Magnesium, mg | 6.4 | 5.12-7.68 | <0.01% | 1.3 |
| Manganese, mg | | | | |
| Molybdenum, mcg | | | | |
| Phosphorus, mg | 40 | 32-48 | <0.01% | 8 |
| Selenium, mcg | | | | |
| Zinc, mg | | | | |
| Potassium, mg | 200 | 160-240 | 0.02-0.02 | 40 |
| Sodium, mg | 380 | 304-456 | 0.03-0.04 | 76 |
| Chloride, mg | 8 | 6.4-9.6 | <0.01% | 1.6 |
| Inositol, mg | | | | |
| L-alanine, mg | 520 | 416-624 | 0.04-0.06 | 104 |
| L-arginine, mg | 1100 | 880-1320 | 0.09-0.13 | 220 |
| L-aspartate, mg | 730 | 584-876 | 0.06-0.09 | 146 |
| L-cysteine, mg | 107.7 | 86-129 | <0.01% | 21.5 |
| L-glutamate, mg | 1600 | 1280-1920 | 0.12-0.19 | 320 |
| L-glycine, mg | 95 | 76-114 | 0.01-0.01 | 19 |
| L-histidine, mg | 250 | 200-300 | 0.02-0.03 | 50 |
| L-isoleucine, mg | 900 | 720-1080 | 0.07-0.10 | 180 |

TABLE 4-continued

Tylactin Restore 10 Citrus
Tylactin Restore 10 Citrus

| Nutrients | per serving 16.9 fl oz (500 mL) | Range | % Weight Range | per 100 mL |
|---|---|---|---|---|
| L-leucine, mg | 2110 | 1688-2532 | 0.16-0.25 | 422 |
| L-lysine, mg | 520 | 416-624 | 0.04-0.06 | 104 |
| L-methionine, mg | 170 | 136-204 | 0.01-0.02 | 34 |
| L-phenylalanine, mg | 16 | 12.8-19.2 | <0.01% | 3.2 |
| L-proline, mg | 1000 | 800-1200 | 0.08-0.12 | 200 |
| L-serine, mg | 640 | 512-768 | 0.05-0.07 | 128 |
| L-threonine, mg | 1400 | 1120-1680 | 0.11-0.16 | 280 |
| L-tryptophan, mg | 150 | 120-180 | 0.01-0.02 | 30 |
| L-tyrosine, mg | 2 | 1.6-2.4 | <0.01% | 0.4 |
| L-valine, mg | 700 | 560-840 | 0.05-0.08 | 140 |

We claim:

1. A shelf-stable, liquid nutritional formula for dietary management of tyrosinemia comprising:
    (a) a protein source that includes:
        (i) caseino-glyco-macropeptide (cGMP); and
        (ii) complementary amino acids which are a mixture of arginine, tryptophan, leucine, histidine and cysteine, wherein the cGMP is between about 3% and about 6% of the total weight of the formula, and wherein the protein source provides 20-35% of the energy of the nutritional formula;
    (b) a fat source which provides 20% to 30% of the energy of the nutritional formula, wherein the fat source is about 1.5% to about 2.2% of the total weight of the nutritional formula;
    (c) a carbohydrate source which provides 40% to 60% of the energy of the nutritional formula,
    (d) octenyl succinate starch (OSS); and,
    (e) a sodium hexametaphosphate-metal (SHMP-metal) mixture comprising SHMP bound to copper and iron, wherein the nutritional formula contains less than 0.01% by weight of tyrosine.

2. The shelf-stable, liquid nutritional formula of claim 1, wherein together the complementary amino acids are about 1.5% to about 2.35% of the total weight of the formula.

3. The shelf-stable, liquid nutritional formula of claim 1, wherein the formula comprises no added tyrosine or phenylalanine.

4. The shelf-stable, liquid nutritional formula of claim 1, further comprising at least one vitamin and at least one mineral, wherein together the at least one vitamin and the at least one mineral are between about 1.5% and about 2.35% of the total weight of the formula.

5. The shelf-stable, liquid nutritional formula of claim 4, wherein the at least one mineral is dicalcium phosphate, calcium lactate, dipotassium phosphate, magnesium citrate, sodium ascorbate, zinc sulfate, calcium d-pantothenate, manganese sulfate, potassium iodide, sodium selenite, sodium molybdate, or chromium chloride, and wherein the at least one vitamin is choline bitartrate, ascorbic acid, niacinamide, vitamin E dl-alphatocopheryl acetate, vitamin A palmitate, vitamin B6 pyridoxine, riboflavin, thiamin hydrochloride, folic acid, vitamin K 1 phytonadione, biotin, vitamin D3 cholecalciferol, or vitamin B12 cyanocobalamin.

6. A shelf-stable, liquid nutritional formula for dietary management of tyrosinemia comprising:
    (a) a protein source that includes:
        (i) caseino-glyco-macropeptide (cGMP); and
        (ii) complementary amino acids which are a mixture of arginine, tryptophan, leucine, and histidine;
    (b) a fat source, wherein the fat source provides between about 18% to about 27% of the total calories in the formula,
    (c) octenyl succinate starch (OSS); and,
    (d) a sodium hexametaphosphate-metal (SHMP-metal) mixture comprising SHMP bound to copper and iron, wherein the protein source provides between about 28% and about 43% of the total calories in the formula, and the formula contains less than 0.01% by weight of tyrosine.

7. The shelf-stable, liquid nutritional formula of claim 6, wherein the formula comprises no added tyrosine or phenylalanine.

8. The shelf-stable, liquid nutritional formula of claim 6, further comprising vitamins and additional minerals, wherein the vitamins and additional minerals are present in an amount sufficient to make the formula nutritionally complete.

9. The shelf-stable, liquid nutritional formula of claim 8, wherein the additional minerals are dicalcium phosphate, calcium lactate, dipotassium phosphate, magnesium citrate, sodium ascorbate, zinc sulfate, calcium d-pantothenate, manganese sulfate, potassium iodide, sodium selenite, sodium molybdate, and chromium chloride, and wherein the vitamins are choline bitartrate, ascorbic acid, niacinamide, vitamin E dl-alphatocopheryl acetate, vitamin A palmitate, vitamin B6 pyridoxine, riboflavin, thiamin hydrochloride, folic acid, vitamin K 1 phytonadione, biotin, vitamin D3 cholecalciferol, and vitamin B12 cyanocobalamin.

10. The shelf-stable, liquid nutritional formula of claim 3, wherein the formula comprises between about 2.4 mg and about 3.6 mg tyrosine.

11. The shelf stable, liquid nutritional formula of claim 7, wherein the formula comprises between about 2.4 mg and about 3.6 mg tyrosine.

* * * * *